United States Patent [19]

Benedict et al.

[11] Patent Number: 5,520,190
[45] Date of Patent: May 28, 1996

[54] CARDIAC BLOOD FLOW SENSOR AND METHOD

[75] Inventors: George J. Benedict, Santa Cruz; Timothy A. Fayram, Gilroy, both of Calif.

[73] Assignee: Ventritex, Inc., Sunnyvale, Calif.

[21] Appl. No.: 331,416

[22] Filed: Oct. 31, 1994

[51] Int. Cl.⁶ .............................. A61B 5/02; G01K 11/20
[52] U.S. Cl. ..................... 128/700; 128/634; 128/612; 374/131; 374/161
[58] Field of Search .................... 607/6, 17, 18, 607/21; 128/700, 713, 634; 374/131

[56] References Cited

U.S. PATENT DOCUMENTS

| | | | |
|---|---|---|---|
| 4,542,987 | 9/1985 | Hirschfeld | 356/44 |
| 4,560,286 | 12/1985 | Wickersheim | 374/131 |
| 4,621,929 | 11/1986 | Phillips | 374/43 |
| 4,688,573 | 8/1987 | Alt | 607/21 |
| 4,729,668 | 3/1988 | Angel et al. | 374/161 |
| 4,752,141 | 6/1988 | Sun et al. | 374/161 |
| 4,986,671 | 1/1991 | Sun et al. | 374/131 |
| 5,005,574 | 4/1991 | Fearnot et al. | 607/21 |
| 5,040,538 | 8/1991 | Mortazavi | 128/633 |
| 5,174,299 | 12/1992 | Nelson | 128/736 |
| 5,336,244 | 8/1994 | Weijand | 607/21 |
| 5,370,667 | 12/1994 | Alt | 607/19 |

*Primary Examiner*—William E. Kamm
*Assistant Examiner*—Carl H. Layno
*Attorney, Agent, or Firm*—Steven M. Mitchell; Mark J. Meltzer

[57] ABSTRACT

A cardiac blood flow sensor includes a light source and a photodetector within a housing. The light source projects a beam through a fiber optic line having a first end optically connected to the housing and a distal tip positioned within the patient's heart. A ruby positioned at the distal tip is heated by the beam, and fluoresces for a period of time after illumination ceases. The period of time depends on the temperature of the ruby, so that the fluorescent light is transmitted back through the optic line to the photodetector. The signal generated by the photodetector may be analyzed to estimate the blood flow rate, due to the thermal effect of blood flowing past the heated ruby. The flow sensor may be contained in a common housing with a defibrillator that is implanted in a patient. The sensor may remain inactive until a tachycardia or rapid heart rate is detected, upon which the light source is activated. The cardiac condition is analyzed based on the detected heart rate and blood flow and, if needed, an appropriate therapy is delivered.

19 Claims, 2 Drawing Sheets

CARDIAC BLOOD FLOW SENSOR AND METHOD

FIELD OF THE INVENTION

This invention relates to implantable cardioverter/defibrillators and more particularly to apparatus and method for discrimination of pathologic tachycardia from physiologic tachycardia.

BACKGROUND AND SUMMARY OF THE INVENTION

The human heart may surlier from two classes of rhythmic disorders or arrhythmias: Bradycardia and tachyarrhythmia. Bradycardia occurs when the heart beats too slowly, and may be treated by a common pacemaker delivering low voltage (about 1 V) pacing pulses. Of concern here is tachyarrhythmia, which involves an abnormally high heart rate between about 100 to 200 beats per minute, but without hemodynamic or blood flow efficiency. Of particular concern is a ventricular tachycardia, in which the ventricles have not completely filled before they contract, thus diminishing the voltime of blood pumped. The pumping inefficiency is generally proportional to the heart rate. A severe form of tachyarrhythmia is fibrillation, which occurs at heart rates of 180 to 300 beats per minute, and involves erratic, disorganized beating that pumps virtually no blood.

Implantable cardioverters/defibrillators (ICD) or pulse generators are used for antitachycardia pacing to correct rapid heart rates by delivering a rapid sequence of pacing pulses of 1 to 10 volts to break the arrhythmia. ICD devices treat severe tachycardia with cardioversion, by delivering a shock of 100 to 750 volts synchronously with the peak of the heart's R-wave signal as detected by an electrocardiogram (ECG). Heart fibrillation receives similar therapy, but the erratic ECG signal may not provide a clear R-wave peak for synchronization.

Normally, the spacing between successive R-wave peaks is used to determine the heart rate. Extremely high or irregular heart rates clearly require therapy. Moderately elevated heart rates may be of ambiguous origin, either from healthy exercise, or from the disorders discussed above. To distinguish between these causes, treatment techniques have included measurement of blood pressure, oxygen saturation, Doppler ultrasound parameters, and ECG morphology. These techniques have limited accuracy and practicality, particularly outside of a clinical setting.

The present invention avoids the limitations of existing techniques and devices by providing a cardiac blood flow sensor that measures blood flow within the heart. The apparatus includes a light source and a photodetector within an implanted housing. The light source projects a beam through a flexible elongated light conduit having a first end optically connected to the housing and having a distal tip positioned within the patient's heart. The distal tip includes a ruby having fluorescent characteristics that vary with temperature. The temperature of the ruby is determined initially from the ruby fluorescence decay time. Then the beam is activated for a period of time to elevate the temperature of the ruby well above the ambient blood temperature. The temperature of the ruby is again determined from its fluorescence decay time. The elevated temperature difference from the initial temperature depends on the cooling effect of the blood flow. The cooling effect is greater during healthy blood flow than during tachyarrhythmia.

The fluorescent light is transmitted back through the conduit to the photodetector, which generates a signal that may be analyzed by a controller to determine whether a tachycardia is physiologic or pathologic in origin.

The flow sensor may be contained in a common housing with a defibrillator that is implanted in a patient. The sensor may remain inactive until a tachycardia is detected, upon which the light source is activated. The defibrillator may be activated only if the flow sensor has detected a blood flow rate below a predetermined level.

DETAILED DESCRIPTION OF A PREFERRED EMBODIMENT

Figure 1:
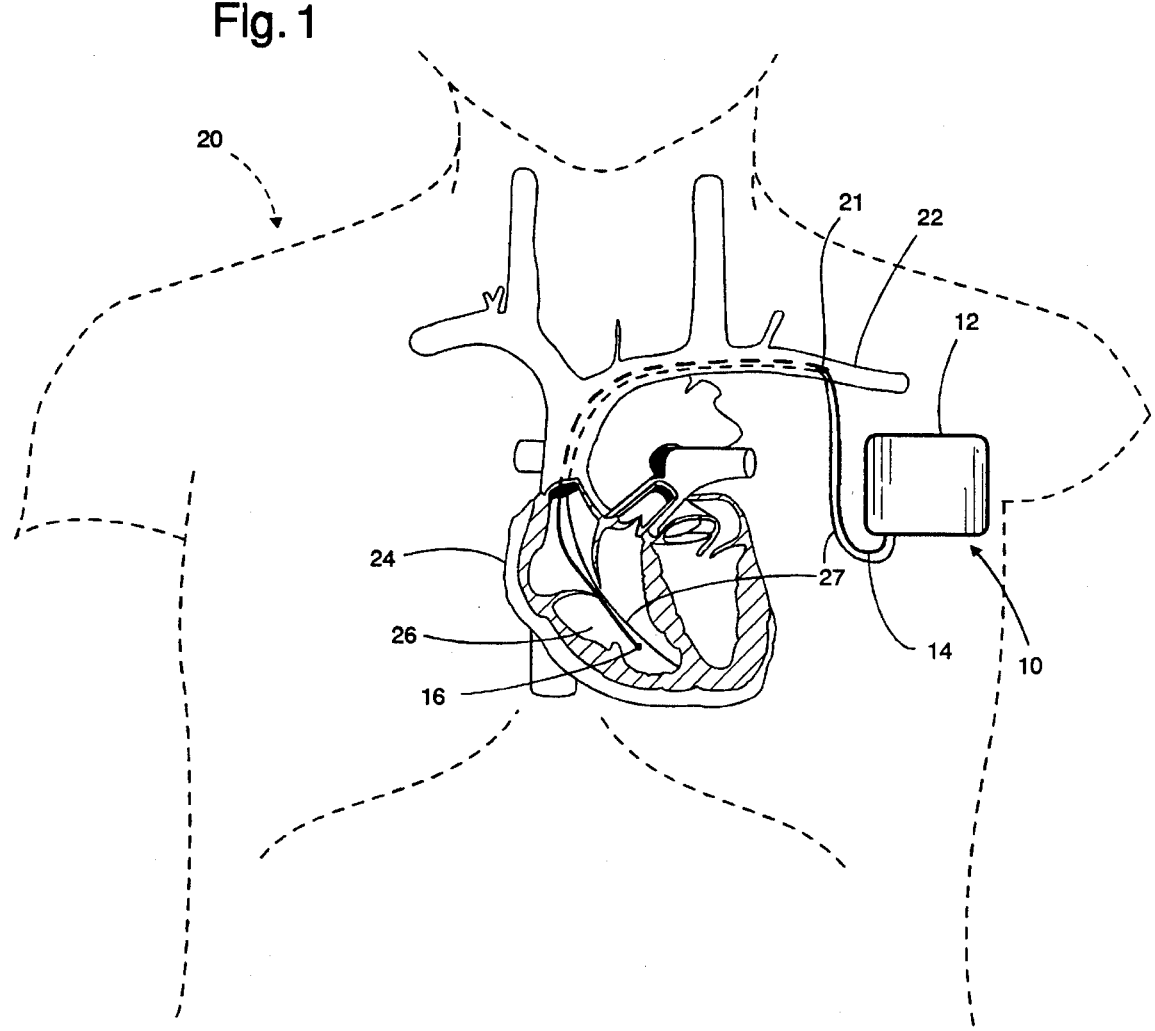
FIG. 1 is an anterior view of a patient implanted with a preferred embodiment of the invention.

FIG. 1 shows an Implantable Cardioverter/Defibrillator (ICD) and flow sensor unit 10, including a single housing 12 and a flexible fiber optic line 14. The optic line serves as a light conduit extending from the housing, and terminates at a distal tip 16. The entire unit 10 is implanted in a patient 20, with the housing 12 located in the patient's pectoral or abdominal region. The optic line 14 extends from the housing to an incision 21 in the patient's subclavian vein 22. The optic line 14 passes through the incision, and extends downwardly through the vein into the heart 24, with the distal tip 16 positioned within the right ventricle 26. The optic line may be secured to a wall of the right ventricle with the distal tip extending away from the wall. This configuration provides an angle that is more likely perpendicular to the direction of blood flow 25, and may thereby improve the efficiency of the system. A sensing/pacing lead 27 extends from the housing 12 into the ventricle 26, and is secured to the apex of the right ventricle using tines or a screw tip. Surgical implantation may be achieved by encasing the optic line 14 in a semi-rigid hollow catheter, which may be inserted transvenously. The catheter is removed alter the line is positioned. The fiber optic line 14 and the sensing/pacing lead 27 may be integrated into a single lead, with each component passing through a respective lumen of a multi-lumen lead, facilitating implantation. Such lead could also include one or more defibrillation conductors, one or more sensing/pacing conductors, and may include an additional lumen through which a stylet may be inserted to facilitate implantation without the use of a catheter. The illustrated embodiment shows separate leads to provide clarity.

Figure 2:
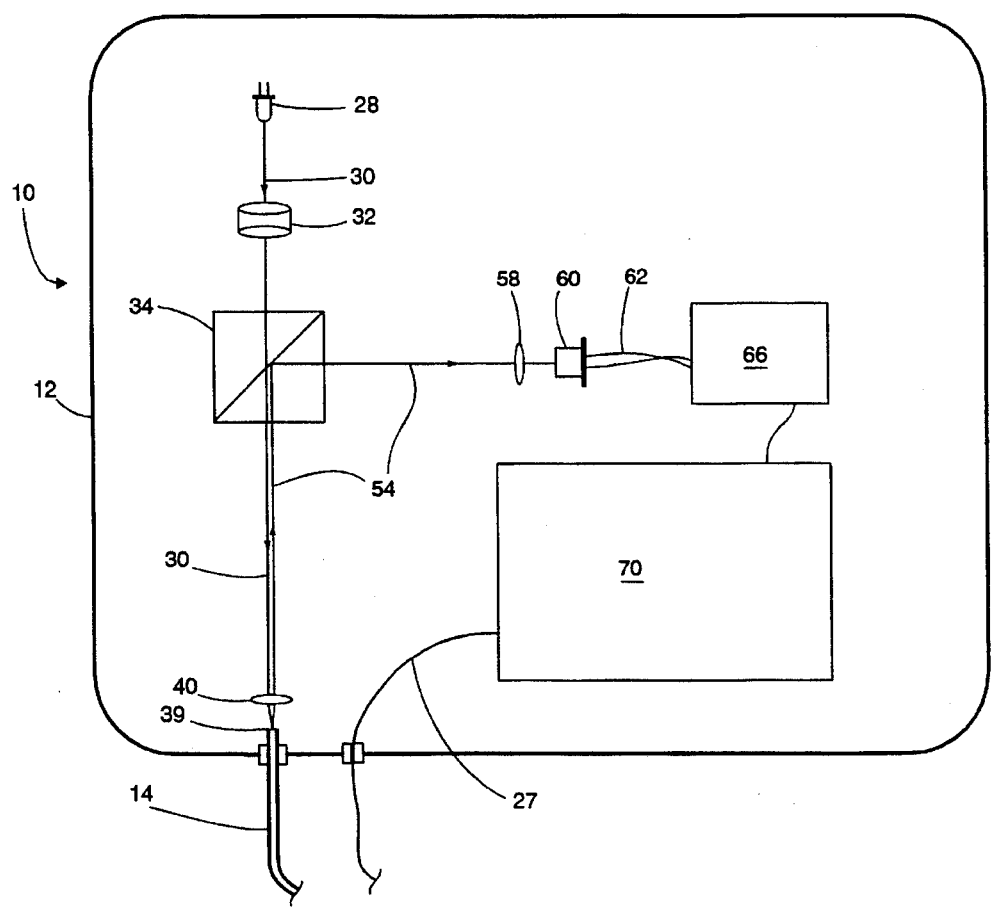
FIG. 2 is a schematic view of the embodiment of FIG. 1.

FIG. 2 shows the ICD and flow sensor unit 10. A green light-emitting diode (LED) 28 emits a beam of light along a first beam path 30, through a collimating lens 32 that generates a beam of parallel rays. The beam then passes through a dichroic beam splitter 34, which transmits the green collimated beam, while reflecting primarily red light wavelengths. The transmitted beam then encounters a concentrating lens 40. A first end 39 of the optic line 14 is positioned at the focal point of tile lens 40, so that the parallel rays of the beam are focused into the core of the optic line 14. The green beam is then transmitted through the line toward the line's distal tip 16.

Figure 3:
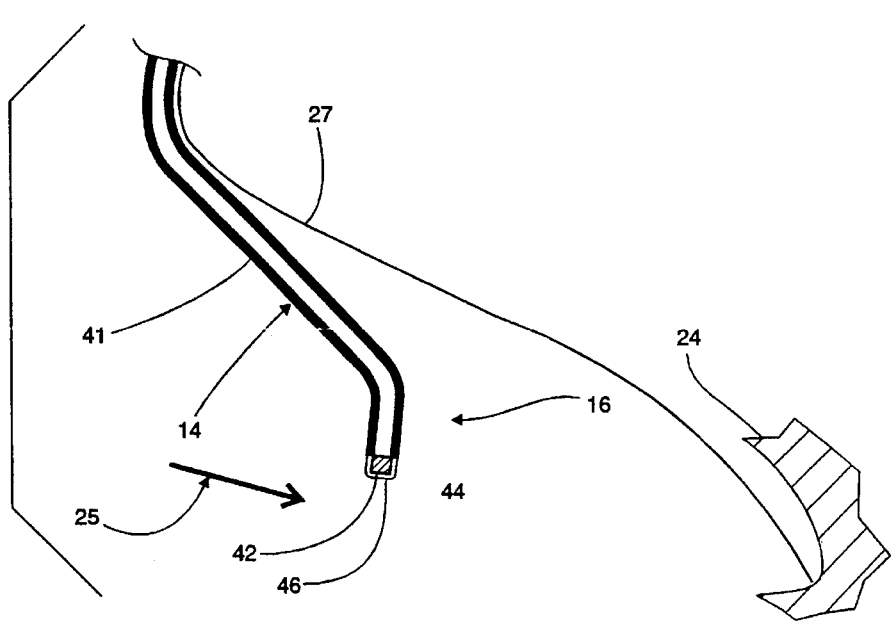
FIG. 3 is an enlarged view of the embodiment of FIG. 1.

FIG. 3 shows the optical details of the distal tip 16 of the optic line 14. The optic line 14 includes a sheath 41 formed of silicone or other biocompatible material to permit long term use in the blood stream. A ruby 42 is positioned over the terminus 44 of the line 14, and is sized so that at least a majority of green light transmitted through the line is intercepted and absorbed by the ruby 42. A protective coating 46 surrounds the ruby, and minimizes tissue growth over time. A portion of the red fluorescent light emitted by the ruby is transmitted back up the optic line 14 to the housing 12. Returning to FIG. 2, the red fluorescent light re-enters the housing 12, and is collimated by lens 40 so that it follows a returning beam path 54. The returning beam encounters the dichroic beam splitter 34, which reflects the red returning beam. The returning beam then passes through a lens 58, which focuses the light onto a silicon photodetector 60 that generates an electrical signal corresponding to the intensity of tile incident light as a function of time. A filter transmitting at 694 nm may be used before or after lens 58 to improve the signal to noise performance of the sensor.

The photodetector has an electrical output line 62 that carries the signal. A processor 66 is connected to line 62, and processes the signal from the photodetector to determine the fluorescence duration, and thereby the temperature, of the ruby before and after heating. From the difference in ruby temperatures, the processor may estimate the blood flow within the ventricle, or at least determine whether the blood flow is likely above or below a predetermined threshold indicating that therapy may be required. The processor is electrically connected to conventional ICD circuitry 70, which provides cardiac therapy by selectably applying a voltage to the connected electrode sensing/pacing lead 27, or to a defibrillation lead electrode (not shown). The lead 27 is capable of sensing the heart rate and providing Brady pacing or antitachycardia pacing. An additional return electrode (not shown) providing a "ground" for the high voltage shocks may be placed in the superior vena cava, or may use the housing of a pectorally implanted device. The therapy provided by the defibrillator is not necessarily a defibrillation shock, but is frequently antitachycardia pacing or a cardioversion shock. The defibrillator includes a heart rate sensor (not shown) that permits activation of the flow sensor light source 28 only when the heart rate exceeds a rate that may be problematic. The device may be programmed to provide therapy only if the flow sensor processor 66 indicates a blood flow below the preselected rate.

The processor 66 or ICD circuitry 70 may also be programmed to apply therapy in response to the satisfaction of more complex conditions. A complex function of the heart rate, measured flow rate, characteristics of the patient, and other interacting variables may be used to determine when therapy is indicated.

The method of operation occurs in a preferred sequence. Basically, a baseline temperature is determined, the ruby is heated, and a second temperature is determined for comparison and analysis. The specific sequence is as follows:

I. Initiation of Operation
  A. If the processor senses a heart rate above a predetermined rate associated with tachyarrhythmia, the operation is initiated.
II. Baseline Temperature Determination
  A. Brief illumination of the LED with an initial excitation pulse of 10 to 100 µsec duration.
  B. Blanking pause of 10 µsec after brief illumination ceases, permitting the LED light to decay to dark after shutoff.
  C. Photodetector measures the decay time of the fluorescence received from the ruby.
  D. Processor integrates the fluorescent signal to determine the fluorescent decay time, and calculates the baseline temperature.
III. Heating of the Ruby
  A. Prolonged illumination or heating pulse of the LED for approximately 1 second.
  B. Blanking pause of 3 msec after brief illumination ceases, permitting dissipation of ruby fluorescence due to the heating pulse.
IV. Second Temperature Determination
  A. Brief illumination of the LED with a final excitation pulse of 10 to 100 µsec duration.
  B. Blanking pause of 10 µsec after brief illumination ceases, permitting the LED light to decay to dark after shutoff.
  C. Photodetector measures the decay time of the fluorescence received from the ruby.
  D. Processor integrates the fluorescent signal to determine the fluorescent decay time, and calculates the second temperature.
V. Analysis and Therapy
  A. Processor compares the baseline and second temperatures to determine whether blood flow is below a predetermined threshold (as would be indicated by a relatively high second temperature due to a lack of cooling blood flow during the heating and subsequent steps.)
  B. If blood flow is below the predetermined threshold, therapy in the form of an electrical pulse delivered via the sensing/pacing lead to the patient's heart.

It is not necessary to obtain an absolute temperature measurement. Only a relative difference between the fluorescent decay times before and after the heating step is needed to determine whether a tachycardia is physiologic or pathologic in origin. The vastly different blood flow characteristics between these two conditions permits useful analysis even with estimates that are accurate only to an order of magnitude, although the apparatus and method disclosed herein may be capable of more accurate measurements than are required. Normal blood flow rates vary among subjects at rest between 4 and 8 liters per minute (L/min); normal rates for exercising subjects (physiologic tachycardia) are about five times higher, typically about 15 to 30 L/min. The blood flow rate for a subject experiencing tachyarrhythmia (pathologic tachycardia) is between 1 and 5 L/min, but generally less than 3 L/min. The difference between the flow rates of physiological and pathological tachycardia is at least about a factor of five, which permits the disclosed method and apparatus to clearly distinguish between these conditions to determine whether to apply therapy.

In the preferred embodiment, the ruby fluoresces red light at about 694 nm, and absorbs green light from 500 to 600 nm. Alternatives to the ruby include any material that has an emission that varies with temperature. These may include Neodymium YAG, Neodymium glass, and fluoroptic materials such as those offered by Luxtron Company of Santa Clara, Calif.

The light source may be provided by a green light-emitting diode emitting light at a wavelength of 500 to 600 nm. Alternatives such as lasers, or other conventional sources emitting at similar wavelengths within the ruby's absorption bands may be used. A laser diode emitting at 780 or 830 nm would be suitable for use with Neodymium YAG and Neodymium glass materials mentioned above.

An alternative embodiment measures the ratio of emitted fluorescent spectral lines to determine the initial temperature and the final temperature of the temperature sensitive element.

The use of the term "light" is not intended to limit the invention to visible wavelengths; a wider range of wavelengths may be used.

The ruby's coating 46 is preferably formed of a material formulated to prevent an accumulation of platelets on the distal tip from blocking the heat transfer path. One suitable coating is Parylene™, from Specialty Coating Systems of Indianapolis, Ind. A coating thickness of 2 μm and coefficient of friction of 0.05 to 0.10 is preferred. The optic line is preferably a large core type having a functional diameter of 0.5 to 2.0 mm, permitting significant light flux for heating the ruby.

While the invention is described in terms of a preferred embodiment, the claims are not intended to be so limited.

We claim:

1. A method for discrimination between a pathologic tachycardia and a physiologic tachycardia in a patient comprising the steps of:

selecting a predetermined threshold indicative of tachycardia;

detecting the patient's heart rate;

comparing said detected heart rate with said predetermined threshold;

in response to detection of a heart rate above said predetermined threshold, illuminating a temperature sensitive element positioned within the patient's blood stream, then sensing the duration of fluorescent light emitted;

heating the temperature sensitive element;

waiting a predetermined period of time following said heating step;

after said predetermined period following the heating of the temperature sensitive element, illuminating the temperature sensitive element and then sensing the duration of fluorescent light emitted to measure the temperature of the temperature sensitive element to obtain a relative measure of blood flow; and determining whether the tachycardia is physiologic or pathologic in origin based on the relative measure of blood flow.

2. The method of claim 1 wherein the step of heating the temperature sensitive element includes projecting light onto the temperature sensitive element.

3. The method of claim 1 wherein the step of measuring the temperature of the temperature sensitive element includes sensing fluorescent light emitted from the temperature sensitive element.

4. The method of claim 1 including the step of comparing emissions of fluorescent light from the temperature sensitive element before and after the heating step.

5. The method of claim 1 including the step of applying electrical therapy to the patient's heart in response to detection of a pathologic tachycardia.

6. An implantable cardiac therapy apparatus comprising:

a housing having a port for transmitting light between the housing interior and exterior;

a light source within the housing and in optical communication with the port, such that at least a portion of light emitted by the light source is transmitted along a first beam path between the light source and the port;

a photodetector having an electrical output, the photodetector being responsive to the intensity of light impinging thereon, the photodetector being positioned within the housing and in optical communication with the port, such that at least a portion of light entering the port is transmitted along a second beam path between the port and the detector to impinge on the photodetector;

a processor connected to the photodetector's electrical output;

a flexible elongated light conduit having a first end optically connected to the housing port, and a distal tip including a temperature sensitive element, such that light from the light source is transmitted through the conduit to the distal tip, and such that at least a portion of any light generated by the distal tip is transmitted to the photodetector to generate a signal;

means for illuminating the temperature sensitive element before heating the temperature sensitive element, then sensing the duration of fluorescent light emitted;

means for waiting a predetermined time after heating the temperature sensitive element, then illuminating the temperature sensitive element and sensing the duration of fluorescent light emitted; and a pulse generator having an input connected to the processor for generating an electric pulse in a lead extending from an output port of the pulse generator.

7. The apparatus of claim 6 wherein the pulse generator is an implantable cardioverter/defibrillator.

8. The apparatus of claim 6 wherein the pulse generator is contained within the housing.

9. The apparatus of claim 6 wherein the temperature sensitive element emits light in proportion to its temperature after excitation with electromagnetic radiation.

10. The apparatus of claim 6 wherein the conduit comprises a fiber optic line.

11. The apparatus of claim 6 wherein at least a portion of the conduit is enclosed by a biocompatible sheath.

12. The apparatus of claim 6 wherein the processor includes means for calculating a blood flow rate.

13. The apparatus of claim 6 including a dichroic beam splitter within the housing and within the first and second beam paths, such that portions of the beam paths are coextensive with each other between the beam splitter and the port, and are separate from each other adjacent the respective light source and photodetector.

14. The apparatus of claim 6 including a heart rate sensor.

15. A method of measuring blood flow in the blood stream of a patient, the method comprising the steps:

determining a first baseline temperature by illuminating a light-emitting temperature sensitive element within the blood stream through a flexible conduit having a distal tip immersed in the patient's blood stream and analyzing light emitted therefrom;

heating the light-emitting temperature sensitive element;

waiting a predetermined time after heating the light-emitting temperature sensitive element;

determining a second temperature by illuminating a light-emitting temperature sensitive element and analyzing light emitted therefrom; and analyzing the temperature change to determine the blood flow rate.

16. The method of claim 15 wherein the step of projecting the light includes stimulating fluorescence of the temperature sensitive element.

17. The method of claim 15 wherein the step of projecting the light includes projecting the light within the patient's heart.

18. The method of claim 15 including the step of detecting the patient's heart rate.

19. The method of claim 18 wherein the step of generating the light occurs in response to a detected heart rate above a preselected rate.

* * * * *